(12) United States Patent
Davis et al.

(10) Patent No.: US 7,481,370 B2
(45) Date of Patent: Jan. 27, 2009

(54) REMOVABLE PATIENT IDENTIFICATION STRAP FOR BLOOD RECIPIENT VERIFICATION

(75) Inventors: Chad Davis, Chicago, IL (US); Jonathan Fairman, Chicago, IL (US)

(73) Assignee: Typenex Medical, L.L.C., Chicago, IL (US)

( * ) Notice: Subject to any disclaimer, the term of this patent is extended or adjusted under 35 U.S.C. 154(b) by 267 days.

(21) Appl. No.: 11/415,574

(22) Filed: May 2, 2006

(65) Prior Publication Data

US 2007/0257113 A1    Nov. 8, 2007

(51) Int. Cl.
*G06F 17/00* (2006.01)
*G06K 7/10* (2006.01)

(52) U.S. Cl. .................... 235/462.01; 235/375; 40/633

(58) Field of Classification Search ............... 235/375, 235/383, 462.01; D14/341; 40/633
See application file for complete search history.

(56) References Cited

U.S. PATENT DOCUMENTS

| | | | | |
|---|---|---|---|---|
| 3,197,899 A | | 8/1965 | Twentier | 40/633 |
| 3,698,383 A | * | 10/1972 | Baucom | 600/584 |
| 4,137,660 A | * | 2/1979 | Dettmann et al. | 40/303 |
| 4,199,882 A | | 4/1980 | Clayman | 40/633 |
| 4,226,036 A | * | 10/1980 | Krug | 40/633 |
| 4,906,025 A | * | 3/1990 | Schreindl | 281/45 |
| 5,653,472 A | | 8/1997 | Huddleston et al. | 283/75 |
| 5,785,354 A | * | 7/1998 | Haas | 283/74 |
| 5,979,941 A | | 11/1999 | Mosher, Jr. et al. | 283/67 |
| 6,663,006 B2 | * | 12/2003 | Mullins et al. | 235/472.03 |
| 7,000,951 B2 | | 2/2006 | Valenti, Jr. | 283/74 |
| 7,240,446 B2 | * | 7/2007 | Bekker | 40/633 |
| 2004/0113421 A1 | | 6/2004 | Penuela et al. | 283/105 |
| 2005/0091896 A1 | | 5/2005 | Kotik et al. | 40/633 |
| 2005/0108912 A1 | * | 5/2005 | Bekker | 40/633 |
| 2005/0184508 A1 | | 8/2005 | Verden et al. | 283/117 |
| 2006/0005441 A1 | | 1/2006 | Riley et al. | 40/633 |
| 2006/0254105 A1 | * | 11/2006 | Chang | 40/633 |

OTHER PUBLICATIONS

Secureline Blood Band Solutions & Surelink Blood Recipient Systems URL: http://www.pdcorp.com/healthcare/blood_bands.html.
Typenex Medical—Blood Transfusion Safety Wristband System URL: http://www.typenex.com/en/.

(Continued)

*Primary Examiner*—Thien M. Le
*Assistant Examiner*—Tuyen K Vo
(74) *Attorney, Agent, or Firm*—Workman Nydegger

(57) ABSTRACT

A blood recipient verification device includes a patient ID label region including a top ID label layer on which information can be imprinted, a bottom layer comprising an image material in underlining registry with the top layer, an elongate strap adjacent the patient ID label region, and an identification label region that is removably attached to either an end of the patient ID label region or an end of the elongate strap. At least a portion of the elongate strap may be transparent so as to provide a window through which information on the bottom layer can be read while protecting such information from being damaged. An adhesive coating may be applied to the same surface as the removable identification labels of the identification label region so that when the labels are affixed to a blood sample collection tube, the labels will not be exposed but be protected.

13 Claims, 8 Drawing Sheets

OTHER PUBLICATIONS

Typenex Medical—Product Overview URL: http://www.typenex.com/en/product/.
Typenex Medical—Product Specifications URL: http://www.typenex.com/en/product/specifications.html.
Typenex Medical—Product Improvements URL: http://www.typenex.com/en/product/improvements.html.
Typenex Medical—Frequently Asked Questions (FAQ) URL: http://www.typenex.com/en/product/faq.html.
Typenex Medical—How to Use URL: http://www.typenex.com/en/use/.
Typenex Medical—Online Tutorial URL: http://www.typenex.com/en/use/tutorial/step1.html.
Typenex Medical—Risk Management/Best Practices URL: http://www.typenex.com/en/risk/.

* cited by examiner

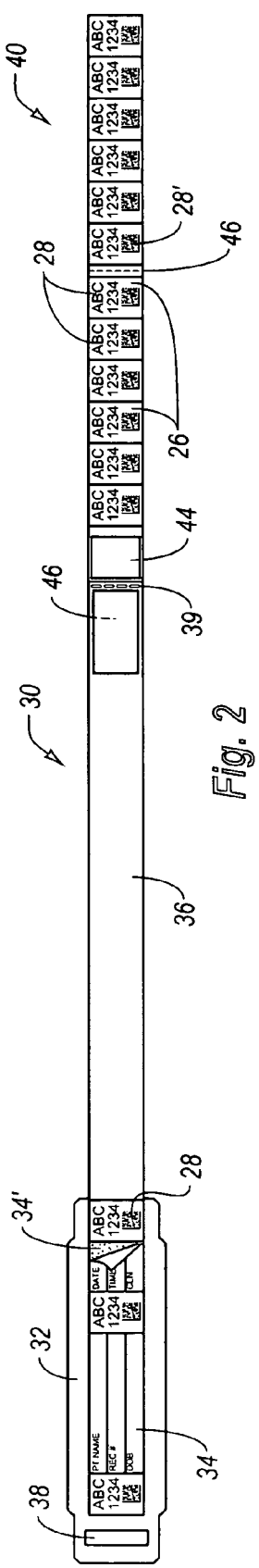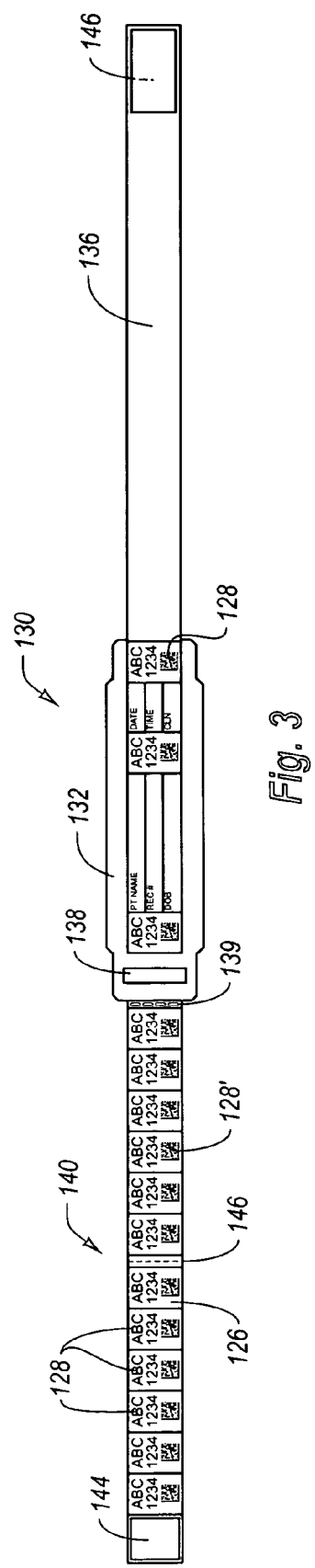

REMOVABLE PATIENT IDENTIFICATION STRAP FOR BLOOD RECIPIENT VERIFICATION

BACKGROUND OF THE INVENTION

1. The Field of the Invention

The invention relates to devices and methods for verifying a blood-recipient and the corresponding units of cross-matched blood to be administered to the blood-recipient.

2. The Relevant Technology

A known blood-recipient verification device is described U.S. Pat. No. 3,698,383, of Baucom, which is incorporated herein by reference. Such a device has been sold commercially under the TYPENEX™.

At the present, donated blood is individualized by hospitals and blood banks. This is usually accomplished by placing on the blood bag or blood collection and storing apparatus a form of identification representing a specific donor. This is done for many reasons, one of which is to provide positive recipient identification or verification, i.e., tying together by some means the recipient, the sample blood from the recipient and the cross-matched blood from a donor or donors to be later transfused. Because errors during handling and verification are in many instances fatal, it is of critical importance that the verification system eliminates to the extent possible any potential for clerical or other errors which could result in a blood transfusion error.

One conventional identification/verification device as seen in FIGS. 1A-1D, includes an identification band 10 and a fastener 12 for use in blood handling procedures. The band 10 includes a tail portion 24, which carries an array of labels 26 bearing identical indicia 28. This unique code 28 is also imprinted one or more times on the opposite end of the band 10, near the fastener 12. The fastener 12 comprises a plastic, clam-shell clip.

In use, the name of the patient and any other suitable information, as desired, are written in a patient ID label area 16 of the band 10. The patient ID label area 16 may comprise a peel-away top layer 18 overlying a bottom layer of image paper 20. The image paper 20 is impregnated with chemical constituents that are capable of interacting to provide a distinct image as a result of pressure impact. In this way, an image of information written on the top layer 18 of label area 16 is directly transferred onto the underlying image paper 20.

After writing information onto the top layer 18 to form an ID label, the technician peels off top layer 18 comprising the ID label, which is then attached to a blood specimen collection tube 14 (e.g., by means of a pressure sensitive adhesive on the backside of the top ID label layer). The image information imprinted on the image paper 20 in the label area remains on the band 10 in patient ID label area 16 (see FIG. 1B).

To attach the identification band 10 to specimen collection to be 14, the technician then peels away a release liner on the backside of the tail 24 of the band 10. The backside of the tail 24 underlying the release liner also carries a pressure-sensitive adhesive, which permits the technician to attach the tail 24 to the collection tube 14 (see FIG. 1B). The array of peel-away labels 26 with the unique identification code 28 is now carried by the blood sample collection tube 14. Because the pressure sensitive adhesive is applied to the backside of the tail 24, the array of peel-away labels 26 necessarily face outward once tail 24 is attached to the blood sample collection tube 14. In other words, labels 26 are exposed and visible once carried by the blood sample collection tube 14, as seen in FIG. 1B.

As seen in FIGS. 1C-1D, the band 10 is then fastened (using the fastener 12) in bracelet fashion around the wrist or the ankle of the patient. Upon fastening, the band 10 is separated along one side of the fastener 12, to release the remainder of the band 10, which remains attached to the blood sample collection tube 14. The identification code 28 remains with the patient, as does the information written on image paper 20 of the band 10 (FIG. 1B). The identification code 28 also remains with the blood sample collection tube 14, as does the information written on top ID layer 18 attached to the collection tube 14.

A sample of blood is collected in the collection tube 14 in conventional fashion. The blood sample within the collection tube 14 is thereafter typed and cross-matched with blood from a donor. When compatible blood from a donor is found through cross matching, one of the peel-away labels 26 on the tail 24 attached to the blood sample collection tube 14 is removed and attached to the blood collection bag containing the donor's blood. The identification code 28 matches the donated blood with the patient to ensure correct matching.

Before administering a blood unit to the patient, the nurse or attendant at bed side or in the operating suite matches the identification code 28 on the patient's bracelet band 10 to the identification code 28 on the label 26 on: the blood bag containing the blood to be transfused. The blood is administered to the patient only upon correspondence of the identification code 28 on the blood bag and the identification code 28 contained on the identification band 10 on the patient.

While the typical procedure is generally successful in eliminating a great deal of potential for clerical or other errors which could result in a blood transfusion error, improvements can still be made. For one, the array of peel-away labels 26 face outward once tail 24 is attached to the blood sample collection tube 14 (see FIGS. 1B and 1C). While this arrangement results in the labels 26 being easily accessible and visible to the nurse or other technician, it does have disadvantages. Because the peelable labels 26 face outward, a significant fraction of them can often become caught in centrifuge equipment or on the edges of a storage rack, particularly when the collection tube 14 is inserted or withdrawn from the centrifuge or storage rack. Not only do such lost labels 26 become unavailable for attachment to blood bags or other use, but because they include a pressure sensitive adhesive it is possible for the labels 26 to accidentally become adhered to another blood collection tube, which introduces the potential (however small) for serious error in the verification process. Another difficulty occurs if the imprinted image information and/or the identification code contained on the bracelet 10 of the patient becomes soiled or otherwise illegible or difficult to recognize.

It would therefore be an advantage to protect this portion of the bracelet so as to further eliminate any potential for clerical or other errors, particularly as any error in correctly matching blood to the correct patient recipient can be life threatening or even fatal.

SUMMARY OF THE INVENTION

The present invention is directed to an improved blood recipient verification device configured as an elongate band. The band includes a patient ID label region including a removable top ID label layer on which information can be directly imprinted. A bottom layer comprising a pressure sensitive image material is in underlining registry with the top layer such that imprinting information in the removable top layer creates an image of the information in the bottom layer. The device also includes (1) an elongate strap adjacent to the patient ID label region and (2) an identification label region that is removably attached to either (a) an end of the patient ID label region or (b) an end of the elongate strap distal to the patient ID label region. The identification label region includes a plurality of removable (e.g., peel away) identification labels, each label bearing identical identification indicia.

Advantageously, the device includes at least one, and preferably both of the following features:

(1) at least a portion of the elongate strap is transparent so that when it is looped through a slot formed in the patient IUD label region, the transparent portion of the strap overlays the remaining bottom layer of the patient ID label region so as to protect image information from being damaged or obliterated, while providing a transparent window through which such information can be read;

(2) the identification label region includes an adhesive coating applied to the same side or surface as the removable identification labels, which advantageously allows the identification label region to be adhered to the blood sample collection tube in a manner so that the plurality of removable identification labels are not outwardly exposed on the exterior of the blood sample collection tube.

In summary, an advantage of forming the portion of the elongate strap that overlays the image information recorded on the image material to be transparent advantageously provides a window through which information can be seen, while protecting information in this area from becoming soiled, difficult to read, or otherwise illegible, which reduces or eliminates the possibility of such an occurrence leading to a cross-matching error. While an opaque strap can still protect the underlying information, such information can only be read by removing the strap from covering the information. This then potentially exposes the information to the destructive forces.

Alternatively, or in addition, locating the adhesive coating on the same surface as the peel-away labels causes the labels to face towards the blood collection tube. In this position it is more difficult for the labels to accidentally catch on equipment. This advantageously prevents the labels from becoming caught in centrifuge equipment, a storage rack, or other equipment where the tube may be inserted into a holder or slot. Because the labels are not exposed at the exterior of the tube, the number of labels that are unintentionally caught and peeled off or otherwise lost or attached to the wrong collection tube is significantly reduced.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIG. 2 is a perspective view of a blood-recipient verification band that embodies features of the invention, wherein the identification label section is attached to an end of the elongate strap;

FIG. 3 is a perspective view of an alternative blood-recipient verification band that embodies features of the invention, wherein the identification label section is attached to an end of the patient ID label region.

DETAILED DESCRIPTION OF THE PREFERRED EMBODIMENTS

I. Introduction

Figure 1A:
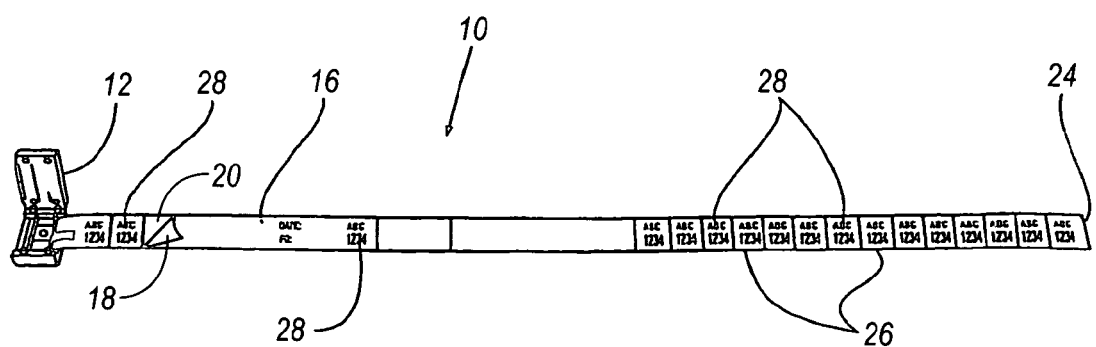
FIGS. 1A-1D are perspective views of a prior art blood-recipient verification device and method.
Figure 1B:
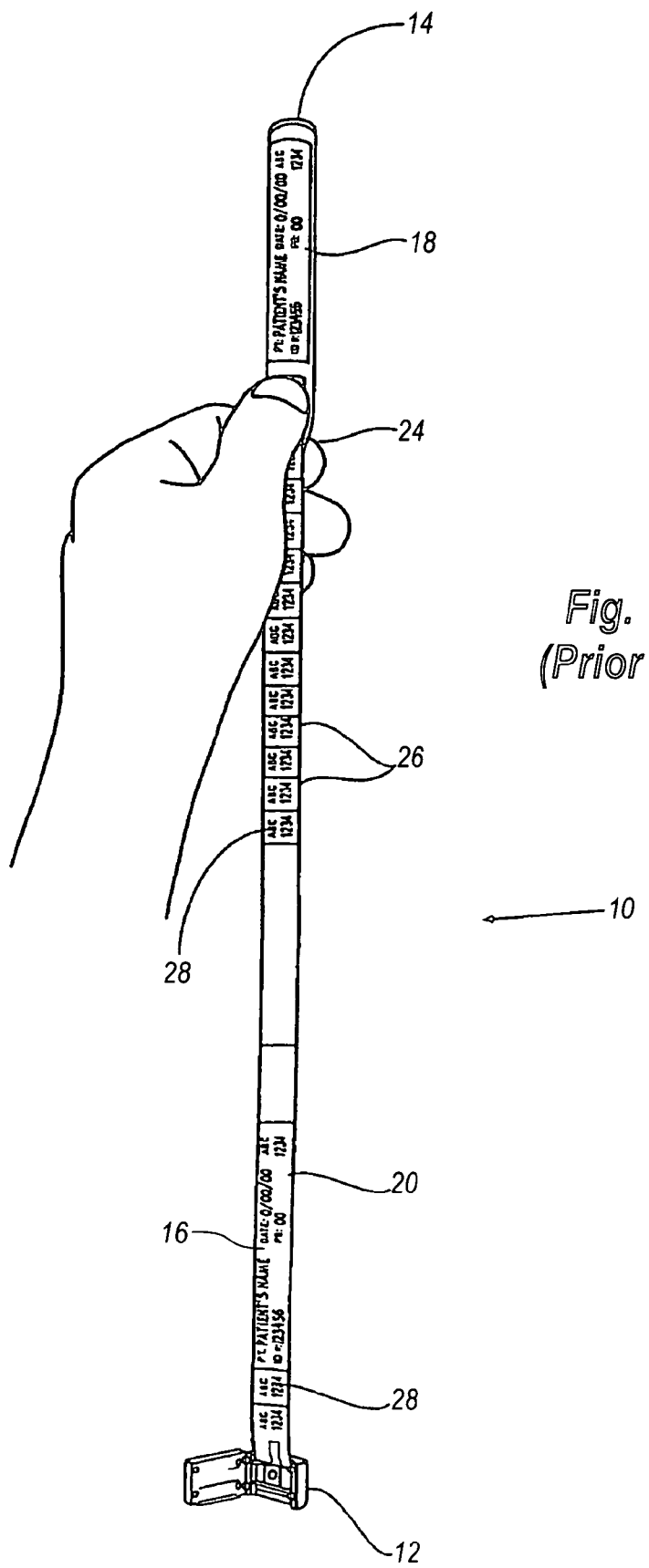
Figure 1C:
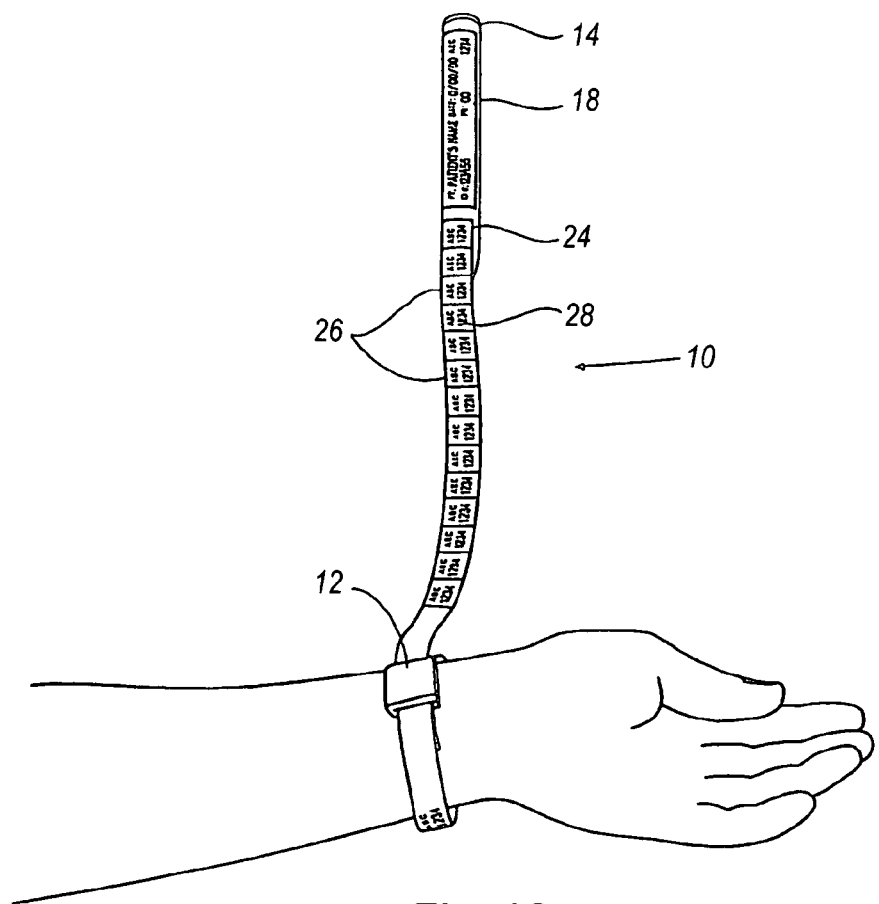
Figure 1D:
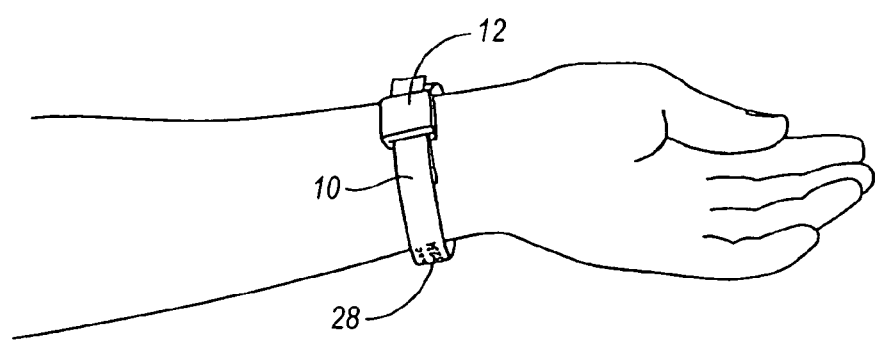

The present invention is directed to a blood recipient verification device configured as an elongate band. The band includes a patient ID label region including a removable top ID label layer in which information can be directly imprinted. A bottom layer comprising a pressure sensitive image material directly underlies the top layer such that information imprinted on the top layer of the ID label creates an image of the information in the bottom layer. The top layer ID label can be peeled away and affixed to a blood sample collection tube, exposing the information recorded on the image material of the bottom layer.

The device also includes an elongate strap adjacent the patient ID label region. The elongate strap is configured to be looped through a slot formed in the patient ID label region so as to form a bracelet. In a preferred embodiment, at least a portion of the strap is transparent such that when the strap is looped through a slot formed in the patient ID label region so as to form a bracelet, the transparent portion overlays the image material on the bottom layer so as to protect the recorded information in this area, while also providing a window through which the information can be read without removing the elongate strap.

The device also includes an identification label region that is removably attached to either an end of the patient ID label region or to a distal end of the elongate strap. The identification label region includes a plurality of peel-away or otherwise removable identification labels, each label bearing identical identification indicia. In a preferred embodiment the labels are disposed on a first surface of the identification label region and an adhesive coating is also disposed on the same first surface of the identification label region, adjacent the plurality of removable identification labels. The adhesive coating (e.g., a pressure sensitive adhesive) is configured to selectively adhere the identification label region to a blood sample collection tube such that the plurality of labels are not outwardly exposed at the exterior of the blood sample collection tube. In other words, locating the adhesive coating on the same surface as the labels results in the labels advantageously facing toward the tube for protection when the strip is affixed to the blood sample collection tube.

II. Exemplary Blood-Recipient Verification Devices

Referring to FIG. 2, a first embodiment of a blood recipient verification device 30 is shown. The device 30 is configured as an elongate band. The device 30 includes a patient ID label region 32 including a peel-away top ID label layer 34 in which information can be directly imprinted by the technician. A bottom layer 34' comprising a pressure sensitive image material is in direct underlying registry relative to top ID label layer 34. Bottom layer 34' is formed of image paper or another substrate that is impregnated with chemical constituents capable of interacting to provide a distinct image as a result of pressure impact. In this way an image of information written on top ID label layer 34 is directly transferred to bottom layer 34'. When the technician peels off the peel-away top ID label layer 34, the image information imprinted on bottom layer 34' remains with the patient ID label region 32. The patient ID region 32 further includes a permanently affixed identification indicia 28 adjacent to the bottom layer 34'.

Device 30 is also illustrated as including a transparent elongate strap 36 that is disposed adjacent to patient ID label region 32. Elongate strap 36 is configured to be looped through a slot 38 formed in patient ID label region 32 so as to form a bracelet that can be fitted over the patient's wrist or ankle. A pressure sensitive adhesive or another adhesive coating may be applied near an end of strap 36 (e.g., the distal end opposite where elongate strap 36 is connected to patient ID label area 32). A peel-away release liner 46 may cover the adhesive so as to protect it until the bracelet 30 is to be fitted over the patient's wrist or ankle. In the illustrated embodiment, the adhesive and release liner 46 are advantageously located on the underside of the band as shown. Advantageously, the width of strap 36 and the width of slot 38 are configured so that slot 38 is just slightly larger in width than strap 36. Also, the width of transparent strap 36 is advantageously configured to be approximately the same (or alternatively slightly larger) as the width of the image material bottom layer 34' on which the patient information is recorded. This ensures that strap 36 covers, and therefore protects, the information on the bottom layer 34'. When looped through slot 38 from below, the transparent elongate strap 36 can be pulled through and positioned so as to cover the patient information located in the image material bottom layer 34' and the adjacent indicia 28, protecting this information from being soiled or otherwise rendered illegible.

An identification label region 40 is removably attached to a distal end of elongate strap 36. Region 40 may comprise a strip having approximately the same width as strap 36. Identification label region 40 is advantageously separable from the elongate strap portion 36 by separation means 39, examples of which include, but are not limited to perforations, rouletting, die cuts, a tearable material (e.g., paper or a thin plastic than can be torn by hand) at the interface of region 40 and strap 36, or other means capable of allowing the technician to tear or otherwise separate region 40 from the remainder of the device 30. Separation means 39 should allow for relatively easy separation by the technician, but should also provide sufficient attachment strength so as to prevent region 40 from becoming prematurely separated from the remainder of device 30. The identification label region 40 includes a plurality of peel-away or otherwise removable identification labels 26, with each label 26 bearing identical identification indicia 28. The illustrated embodiment of each label 26 further includes a machine readable two-dimensional barcode 28'. Such a machine readable mark advantageously allows for the label to be recognized or read by a machine (e.g., by a scanner).

An adhesive coating (e.g., a pressure sensitive adhesive) is covered by a release liner 44 at one end of identification label region 40. The adhesive coating and release liner 44 are advantageously applied to the same surface of region 40 (i.e., the "top" surface) as the array of labels 26. This is opposite the position of illustrated release liner 46 and underlying adhesive coating, which are applied to the "bottom" surface. The location of both the adhesive coating below liner 44 and labels 26 on the same surface is particularly advantageous as it allows the strip of labels to be affixed to a blood sample collection tube such that the labels are not exposed on the exterior of the tube. In other words, when affixed, the labels face 26 towards the tube, where they are not exposed but are rather protected from being caught on an edge or a holding device, for example. This configuration of the labels relative to the tube will be explained in further detail below in conjunction with FIGS. 4G and 4H.

FIG. 3 illustrates an alternative embodiment of a blood recipient verification device 130 including a patient ID label region 132, a transparent elongate strap 136, and an identification label region 140. The principle difference between the embodiments of FIGS. 2 and 3 is that identification label region 140 is removably attached (i.e., by separation means) to an end of patient ID label region 132 in the embodiment of FIG. 3, while identification label region 40 of the device in FIG. 2 is removably attached to a distal end of elongate strap 36. Locating the identification label region 140 adjacent to patient ID label region 132 is advantageous as only the elongate strap 136 must be looped through the slot 138 formed at the far end of patient ID label region 132. In the embodiment of FIG. 2, both the elongate strap 36 and the attached identification label region 40 must be fed through slot 38, which requires additional effort. Furthermore, the embodiment of FIG. 2 prevents attachment of a blood sample collection tube prior to feeding elongate strap 36 through slot 38, as it would interrupt the positive physical connection of all phlebotomy components (i.e., the patient, a blood sample collection tube and its contents, and the blood recipient verification device) prior to drawing a sample of the patient's blood (i.e., identification label region 40 has to be separated from the remainder of device 30 prior to fastening device 30 around the patient's wrist or ankle). In other words, the embodiment of FIG. 3 allows attachment of a blood sample collection tube to identification label region 140 prior to fastening the device around the patient's wrist or ankle, while also preserving the positive physical connection of all phlebotomy components.

III. Exemplary Method of Use

Figure 4A:
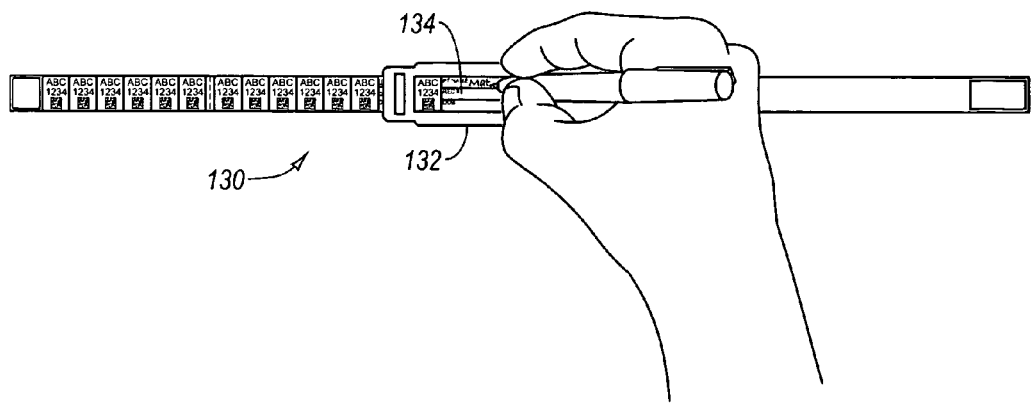
FIGS. 4A to 4H are perspective views showing a method of using the blood-recipient verification band shown in FIG. 3.
Figure 4B:
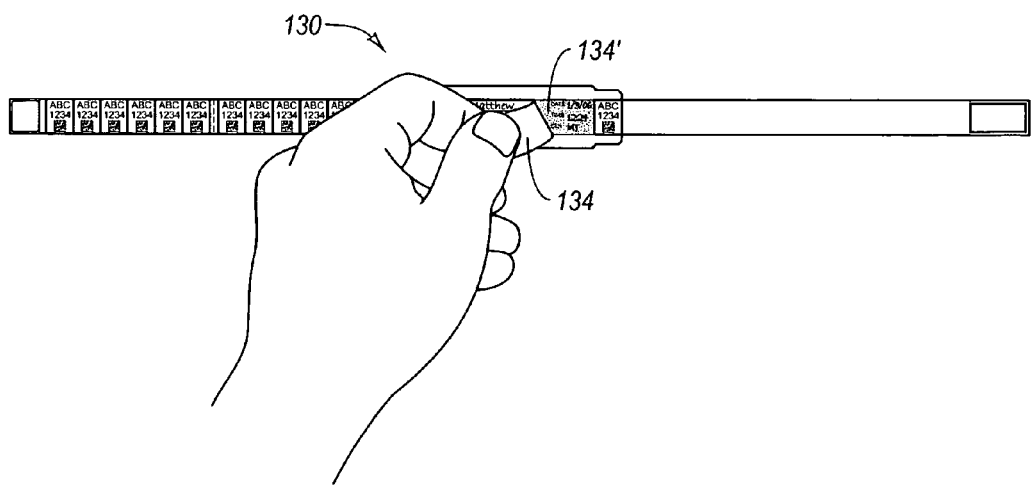
Figure 4C:
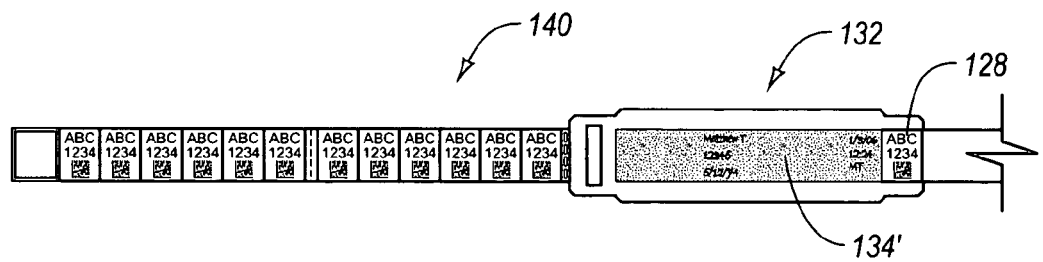
Figure 4D:
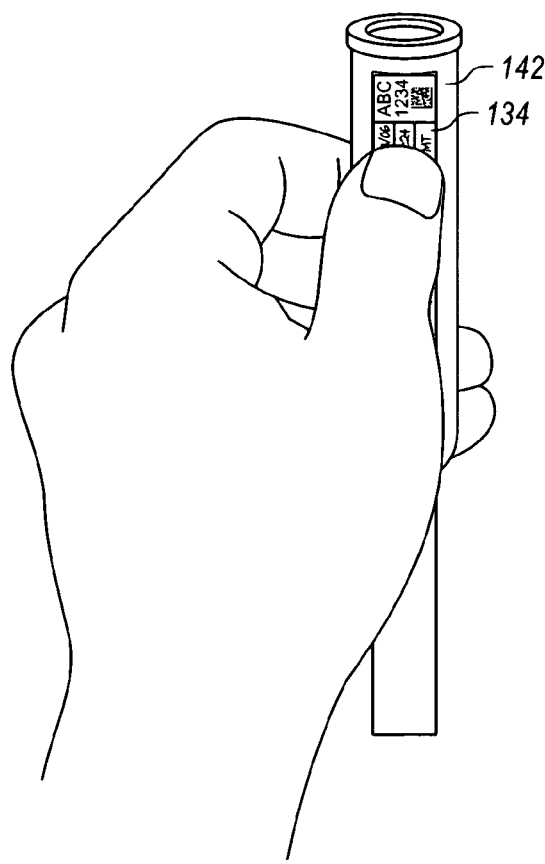

In use and as seen in FIGS. 4A-4H, the name of the patient and any other suitable information, as desired, is written onto top ID label layer 134 of patient ID label region 132 (see FIG. 4A). The top ID label layer 134 comprises a peel-away label (see FIG. 4B) or other removable layer directly overlying a bottom layer 134' comprising image paper or another image material substrate that is impregnated with chemical constituents capable of interacting to provide a distinct image as a result of pressure impact. In this way an image of information written on top layer 134 is directly transferred to bottom layer 134'. When the technician peels off the top ID label layer 134 as seen in FIG. 4B, the image information imprinted on image material of bottom layer 134' remains on the elongate band device 130 as seen in FIG. 4C. The peel away top ID label 134 is subsequently attached to a blood sample collection tube 142 (see FIG. 4D). Top ID label 134 carries, for example, a pressure sensitive adhesive on its underside for this purpose.

Figure 4E:
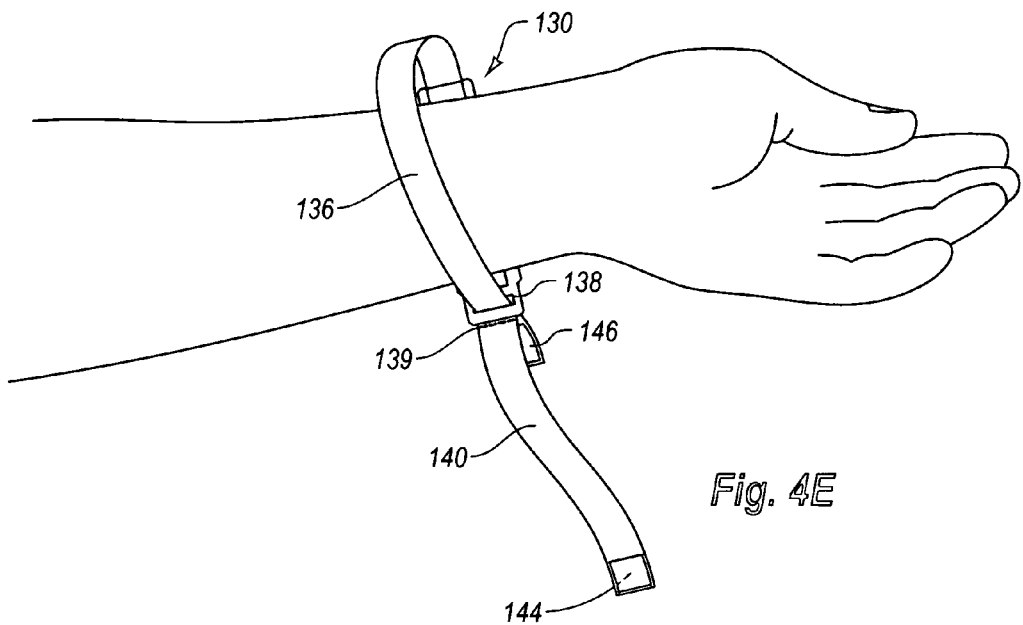

As FIG. 4E shows, the elongate band 130 is fastened in bracelet fashion around the wrist or ankle of the patient. The far end of elongate strap 136 bearing a release liner 146 over a pressure sensitive adhesive is looped through slot 138. After looping the elongate strap through slot 138 to form a bracelet, the release liner 146 may be removed and the pressure sensitive adhesive underlying liner 146 is used to affix strap 136 over patient ID label region 132 (FIG. 4F).

Figure 4F:
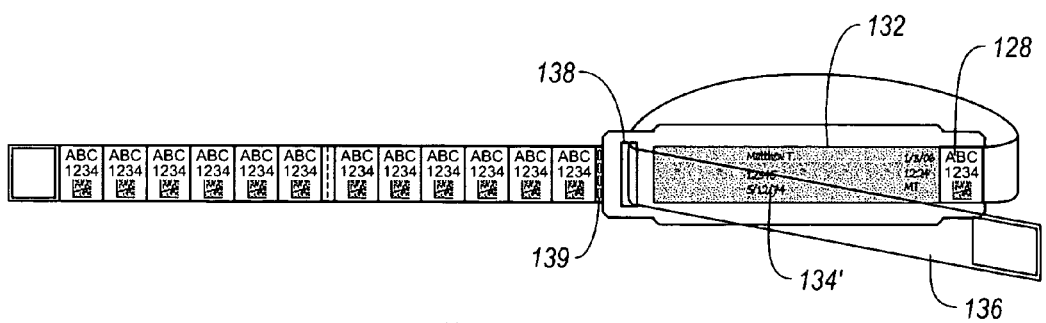

FIG. 4F illustrates in close up how the transparent portion of the elongate strap 136 loops through slot 138 so as to advantageously protect the image information recorded on bottom layer 134' and the identification indicia 128 of patient ID label region 132. The width of elongate strap 136 is advantageously configured to be approximately the same as, or greater than, the width of the image paper or image substrate bottom layer 134'. In this way, the strap 136 will entirely cover the information on bottom layer 134'. Protecting the image information on the bracelet portion that is attached to the patient is particularly advantageous as it minimizes the potential for errors due to soiling or other events resulting in this information becoming illegible or otherwise unrecognizable.

Exactly where the pressure sensitive adhesive underlying liner 146 is affixed along the continuous length of patient ID label region 132 or strap 136 depends on the size of the patient's wrist or ankle and the diameter of the formed bracelet. Generally, the end of strap 136 is adhered so as to form an appropriately sized bracelet in which the transparent portion of the strap 136 covers the information recorded on image material of bottom layer 134' and the identification code 128 bearing the indicia unique to that band device 130.

The elongate band device 30 or device 130 may be provided in a plurality of lengths and sizes so as to better accommodate, for example, an appropriate bracelet diameter for use with child patients and adult patients. An exemplary band configured for use with a typical adult may have a total length of about 18¼ inches, where the elongate strap and patient ID label area (i.e., those portions forming the bracelet) may have a total length of about 11½ inches. The remaining 6¾ inch length comprises the separable identification label region.

Figure 4G:
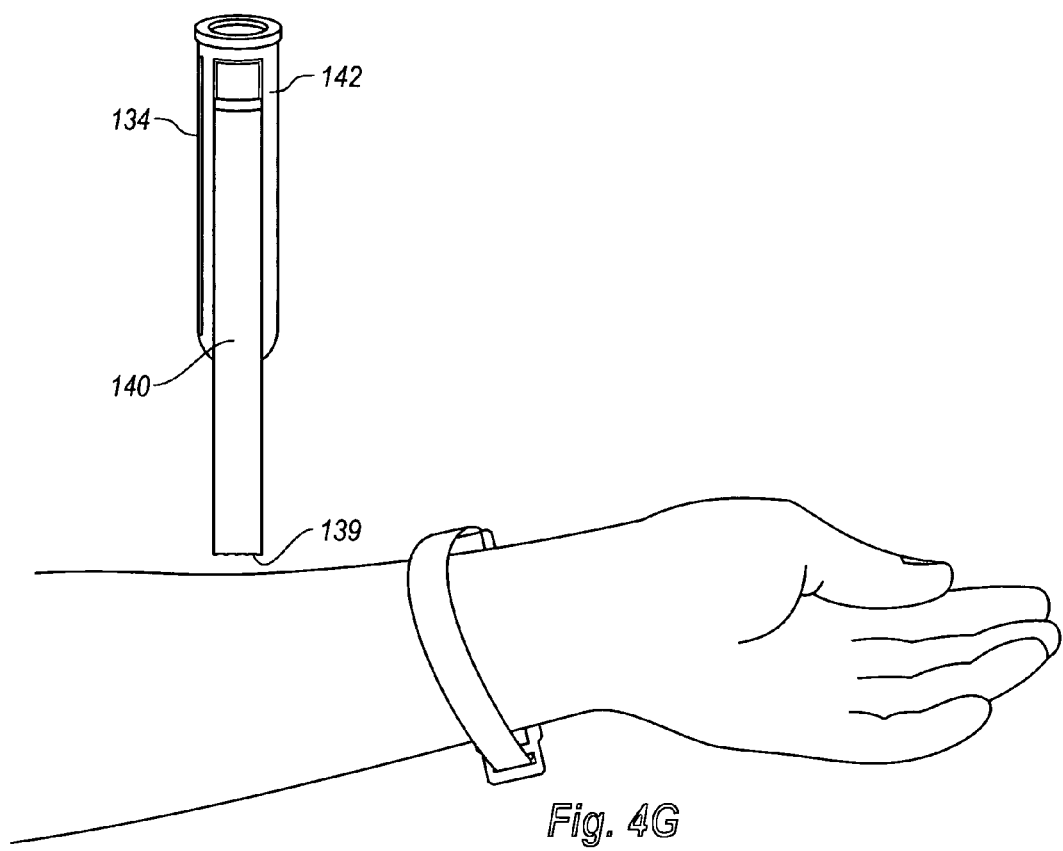

To adhere the identification label region 140 to the blood collection tube 142 (FIG. 4G), the technician peels away release liner 144 from identification label region 140, exposing the adhesive coating (e.g., a pressure sensitive adhesive) underneath, which is advantageously applied to the same surface (i.e., the top surface) as the labels 126 of identification label region 140. As shown in FIG. 4G, the adhesive coating permits the technician to attach identification label region 140 to collection tube 142 in a manner so that labels 126 face toward the tube 142. Orientation in this direction provides protection to the labels 126 throughout subsequent procedures as the tube 142 and label region 140 may be spun in a centrifuge and/or stored in a storage rack. This orientation serves to prevent the labels from inadvertently catching on edges of the equipment and being lost, or even becoming adhered to the blood sample collection tube of another patient (which could lead to a fatal cross-matching error). Although the bracelet may be attached around the wrist of the patient prior to attaching the blood sample collection tube to the elongate band, it shall be appreciated that the bracelet may be attached before or after the blood sample collection tube has been affixed. Technicians may find it easier to first attach the bracelet to the patient, as the tube does not hinder bracelet attachment if not yet attached. In one embodiment, the blood sample collection tube 142 may be provided pre-affixed to the identification label region 140 of the device 130.

Once the bracelet 130 is fastened and tube 142 is affixed to identification label region 140, a positive physical connection has been achieved between the patient and the blood sample collection tube 142. In other words, the method results in the blood sample collection tube being identified with the patient, and minimizes the possibility of clerical errors misidentifying the blood sample collection tube (and it's contents when filled) with the wrong patient because of the positive physical connection of the tube with the patient. At this point, identification label region 140 and blood sample collection tube 142 may be separated from the patient and the bracelet 130 by tearing or otherwise separating the strip 140 along separation means 139. The identification code 128 remains with the patient (at or adjacent the image in bottom layer 134'), and it also remains with blood sample collection tube 142.

Figure 4H:
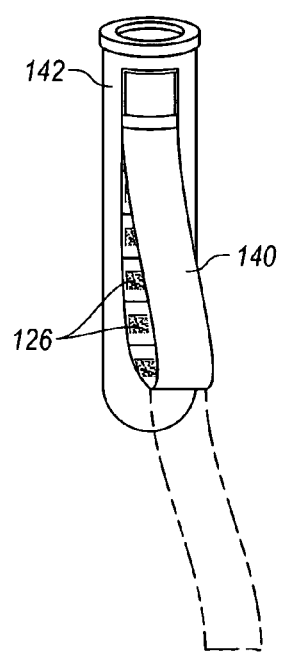

As shown in close up in FIG. 4H, the configuration of the pressure sensitive adhesive on identification label region 140 which is disposed on the same "top" surface as removable labels 126 protects labels 126 when the identification label region 140 is affixed to blood sample collection tube 142. This is so because the labels 126 are not exposed at that exterior of tube 142. Furthermore, as illustrated in FIG. 4H if the strip-like label region 140 is sufficiently long to extend past the end of tube 142, it is particularly advantageous to fold under the end portion of strip 140 so that labels 126 face each other. This provides additional protection to the labels where the tube 142 is shorter than the length to which strip 140 extends. This provides further protection to the labels when the combination of the tube 142 and the strip of labels 140 are inserted within a centrifuge or inserted within a rack or other equipment for holding the tube. This configuration advantageously prevents the labels 126 from being unintentionally peeled off when they come in contact with edges (e.g., a slot on the centrifuge into which the tube is inserted or a slot of a tube storage rack into which the tube is inserted for storage). As perhaps best seen in FIGS. 2 and 3, a fold line 46, 146 may be provided for facilitating folding of the strip as described above. The fold line 46, 146 may comprise a crease, rouletting, perforations, or die cutting of the substrate underlying labels 126. In the illustrated embodiment, fold line 46, 146 is advantageously located at approximately the mid-point of identification label region 140 so that when folded, each label 126 faces another. In any case, folding provides a configuration where at least a portion of labels 126 face another portion of other labels 126 such that none of the labels are exposed at the exterior of the blood sample collection tube 142.

A sample of blood from the patient may then be collected in tube 142 in conventional fashion. The patient recipient's blood sample within tube 142 is thereafter typed and cross matched with blood from a donor. Cross matching may be accomplished in the usual manner. Typically, the donor's blood will be stored for transfusion within a blood collection bag. When compatible blood from a donor is found through cross matching, one of the peel away labels 126 attached to tube 142 is removed and attached to the blood collection bag containing the donor's blood. Because it is generally the practice to setup multiple units of blood for each patient, a plurality of peel away labels 126 is advantageously provided on identification label region 140. The blood is administered to the patient only upon correspondence of the identification code 128 on the blood bag and the identification code 128 on the bracelet of the patient.

It will be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A blood-recipient verification device for use in matching blood between a donor and recipient, comprising:
   an elongate body;
   a patient ID label region along a portion of the elongate body, the patient ID label region further including:
   a removable top ID label layer on which information can be directly imprinted;
   a bottom layer initially beneath the removable top ID label layer comprised of an image material such that imprinting information on the removable top ID label layer creates an image of the information in the bottom layer; and
   a slot through the patient ID label region;

an elongate strap along a portion of the elongate body adjacent to the patient ID label region, at least a portion of the elongate strap comprising a transparent portion, an end of the elongate strap being configured to be looped through the slot through the patient ID label region so as to form a bracelet wherein at least a portion of the transparent portion of the elongate strap overlays the bottom layer so as to protect image information on the bottom layer; and an identification label region along a portion of the elongate body removably attached to either (i) an end of the patient ID label region or (ii) an end of the elongate strap distal to the patient ID label region, the identification label region including one or more removable identification labels.

2. A blood-recipient verification device as recited in claim 1, wherein the patient ID label region further includes an identification indicia.

3. A blood-recipient verification device as recited in claim 2, wherein the one or more removable identification labels have identification indicia thereon that is identical to the identification indicia on the patient ID label region.

4. A blood-recipient verification device as recited in claim 3, wherein the identification indicia on the patient ID label region and the one or more removable identification labels comprises a machine readable code.

5. A blood-recipient verification device as recited in claim 1, wherein the identification label region is removably attached to the end of the patient ID label region.

6. A blood-recipient verification device as recited in claim 1, further comprising separation means for facilitating removal of the identification label region from a remaining portion of the elongate body.

7. A blood-recipient verification device as recited in claim 6, wherein the separation means comprises at least one of perforations, roulettes, die cuts, or a tearable material at an interface between the identification label region and the remaining portion of the elongate body.

8. A blood-recipient verification device as recited in claim 1, the identification label region further comprising an adhesive applied on a same surface as the one or more removable identification labels.

9. A blood-recipient verification device as recited in claim 1, the elongate strap further comprising an adhesive near an end distal to the patient ID label region for affixing the elongate strap to the portion of the elongate body adjacent to the patient ID label region to form a bracelet.

10. A blood-recipient verification device for use in matching blood between a donor and recipient, comprising:
    an elongate body;
    a patient ID label region along a portion of the elongate body, the patient ID label region further including:
        a removable top ID label layer on which information can be directly imprinted;
        a bottom layer initially beneath the removable top ID label layer comprised of an image material such that imprinting information on the removable top ID label layer creates an image of the information in the bottom layer; and
        a slot through the patient ID label region;
    an elongate strap along a portion of the elongate body adjacent to the patient ID label region, an end of the elongate strap being configured to be looped through the slot through the patient ID label region so as to form a bracelet; and
    an identification label region along a portion of the elongate body removably attached to either (i) an end of the patient ID label region or (ii) an end of the elongate strap distal to the patient ID label region, a first surface of the identification label region including one or more removable identification labels and an adhesive coating adjacent to the one or more removable identification labels so as to allow adhesion of the identification label region to a blood sample collection tube in order that the one or more removable identification labels are not outwardly exposed relative to the blood sample collection tube.

11. A blood-recipient verification device as recited in claim 10, further comprising a predetermined fold line approximately disposed at a mid-point of the identification label region in order to facilitate folding under of the identification label region when attached to the blood sample collection tube.

12. A blood-recipient verification device as recited in claim 10, further comprising separation means for facilitating removal of the identification label region from a remaining portion of the elongate body.

13. A blood-recipient verification device as recited in claim 10, wherein at least a portion of the elongate strap comprises a transparent portion such that when an end of the elongate strap is looped through the slot through the patient ID label region so as to form the bracelet, at least a portion of the transparent portion of the elongate strap overlays the bottom layer so as to protect image information on the bottom layer.

* * * * *